United States Patent [19]

Lew et al.

[11] Patent Number: 4,608,204

[45] Date of Patent: Aug. 26, 1986

[54] PROCESS FOR THE PREPARATION OF A LOW VISCOSITY ALKYL TOLUENE OR ALKYL XYLENE SULFONATE

[75] Inventors: Henry Y. Lew; Alan E. Straus, both of El Cerrito, Calif.

[73] Assignee: Chevron Research Company, San Francisco, Calif.

[21] Appl. No.: 797,588

[22] Filed: Nov. 13, 1985

Related U.S. Application Data

[63] Continuation-in-part of Ser. No. 625,923, Jun. 29, 1984, abandoned, which is a continuation of Ser. No. 546,807, Oct. 31, 1983, abandoned.

[51] Int. Cl.$^4$ .................... C07C 143/24; C09K 3/00
[52] U.S. Cl. ........................ 260/505 N; 252/8.55 D
[58] Field of Search ..................... 260/505 N, 513 T; 252/8.55 D

[56] References Cited

U.S. PATENT DOCUMENTS

| 1,396,320 | 11/1921 | Cole | 260/505 N |
| 2,673,207 | 3/1954 | Trusler | 260/505 N |
| 2,961,403 | 11/1960 | Blumer | 260/505 N |
| 4,265,308 | 5/1981 | Hedges et al. | 252/8.55 D |
| 4,425,246 | 1/1984 | Holzwarth et al. | 252/8.55 D |

*Primary Examiner*—Alan Siegel
*Attorney, Agent, or Firm*—T. G. DeJonghe; C. J. Caroli

[57] ABSTRACT

A process for the preparation of a low viscosity aqueous alkyl toluene or alkyl xylene sulfonate which comprises neutralizing alkyl toluene or alkyl xylene sulfonic acid with aqueous sodium hydroxide in the presence of sufficient sodium chloride to lower the viscosity of the sulfonate salt produced. Alternatively, the sodium chloride may be added subsequent to neutralization of the sulfonic acid.

18 Claims, No Drawings

4,608,204

PROCESS FOR THE PREPARATION OF A LOW VISCOSITY ALKYL TOLUENE OR ALKYL XYLENE SULFONATE

CROSS REFERENCE TO RELATED APPLICATIONS

This application is a continuation-in-part of application Ser. No. 625,923, filed June 29, 1984, now abandoned, which is a continuation of application Ser. No. 546,807, filed Oct. 31, 1983, now abandoned.

BACKGROUND OF THE INVENTION

The present invention relates to a process for the preparation of a low viscosity alkyl toluene or alkyl xylene sulfonate.

Alkyl toluene and alkyl xylene sulfonates have utility as surfactants for use in enhanced oil recovery. However, these sulfonates are often highly viscous and therefore can be difficult to handle and transport except in highly dilute form. Since the selection of a particular surfactant which can be utilized in petroleum recovery techniques is based in part upon economic considerations, it would be advantageous to have a method for obtaining a low viscosity alkyl toluene or alkyl xylene sulfonate.

U.S. Pat. No. 3,957,671 describes a low viscosity detergent acid mix containing alkyl benzene sulfonic acid which is prepared by sulfonating alkyl benzene in the presence of benzoic acid.

SUMMARY OF THE INVENTION

The present invention provides a process for the preparation of a low viscosity aqueous alkyl toluene or alkyl xylene sulfonate from the alkyl toluene or alkyl xylene sulfonic acid obtained by the sulfur trioxide sulfonation of alkyl toluene or alkyl xylene having an average molecular weight of about 300 to 365 and a straight or branched alkyl side chain ranging from about $C_{12}$ to $C_{24}$ which comprises neutralizing the alkyl toluene or alkyl xylene sulfonic acid with aqueous sodium hydroxide in the presence of sufficient sodium chloride to lower the viscosity of the aqueous sodium alkyl toluene or alkyl xylene sulfonate produced to less than about 600 centipoise (cp), while maintaining a homogeneous mixture.

In an alternate embodiment of the present invention, the sodium chloride is added subsequent to neutralization of the sulfonic acid to provide the low viscosity sulfonate.

Among other factors, the present invention is based on the discovery that the viscosity of the sodium alkyl toluene or alkyl xylene sulfonate produced by the sulfur trioxide sulfonation and caustic neutralization of alkyl toluene or alkyl xylene can be substantially lowered by the addition of sodium chloride during or subsequent to the neutralization. This is particularly surprising in view of the known teaching that salt water increases the viscosity of petroleum sulfonates. See, for example, U.S. Pat. No. 3,587,737.

DETAILED DESCRIPTION OF THE INVENTION

The alkyl toluene or alkyl xylene employed in the process of the present invention is, in general, a broad-range alkyl toluene or alkyl xylene having an average molecular weight of about 300 to 365, preferably about 310 to 355, and an alkyl side chain ranging from about $C_{12}$ to $C_{24}$, preferably from about $C_{15}$–$C_{20}$. The alkyl toluene or alkyl xylene is normally prepared by the alkylation of toluene or xylene with an appropriate olefin. The alkylate so produced is then sulfonated and neutralized in accordance with the present process.

The alkyl side chain on the toluene or xylene may be straight, i.e., linear, or branched chain in structure and will generally contain from about 12 to about 24 carbon atoms, preferably from about 15 to about 20 carbon atoms. These side chains are derived from corresponding straight or branched chain olefins. Straight chain olefins may be obtained by various procedures known to the art, such as thermal cracking of paraffin waxes and the ethylene growth process. Branched chain olefins are normally obtained by the oligomerization of low molecular weight olefins such as propylene and butylene. Preferred branched chain olefins are propylene oligomers in the $C_{12}$ to $C_{24}$ range. The straight and branched chain olefins are then employed to alkylate the toluene or xylene, using a variety of catalysts known to the art.

The aromatic compound alkylated may be either toluene or xylene. When xylene is employed, any of the three ortho, meta and para isomers of xylene may be utilized, although a mixed xylene is generally preferred.

The alkyl toluene or alkyl xylene is then prepared by alkylating toluene or xylene with the desired olefin in the presence of a Friedel-Crafts catalyst, such as hydrogen fluoride or aluminum chloride. Other Friedel-Crafts catalysts which may be used include sulfuric acid, phosphoric acid, boron trifluoride, and the like. The temperature for the alkylation will ordinarily be in the range of about 0° C. to 60° C. Generally, about 2 to 10 moles, and preferably 5 to 7 moles, of toluene or xylene may be employed per mole of olefin. The alkylate product is isolated by separating the hydrocarbon phase, washing it and distilling out excess toluene or xylene and low molecular weight alkylate to obtain a bottoms product. In the alkylate so produced, the alkyl group may be found in any position on the aromatic ring.

The alkyl toluene or alkyl xylene is then sulfonated with sulfur trioxide to give the corresponding alkyl toluene or alkyl xylene sulfonic acid. The sulfonation is generally accomplished using thin-film dilution techniques, although other types of sulfonation reactors may be used with equivalent results. These include low temperature solvent systems, jet impact and hydrocarbon diluent techniques. Basically the procedure in a film reactor comprises introducing the sulfonate precursor at the top of a reaction vessel such that a thin film is formed on the walls of the vessel. The film is continuously exposed to a gaseous sulfonating agent as the film moves along the surface of the reaction vessel. The sulfonating agent may be sulfur trioxide or sulfur trioxide diluted with a gas which is inert in the process. Preferably, the sulfonation is carried out with sulfur trioxide, using air or nitrogen as a carrier gas.

The alkyl toluene or alkyl xylene sulfonic acid is subsequently neutralized to the sodium salt with aqueous sodium hydroxide in the presence of sufficient sodium chloride to lower the viscosity of the sulfonate produced. In general, about 2 to 10, preferably 3 to 6, weight percent aqueous sodium hydroxide is suitable for neutralizing the sulfonic acid. Alternatively, the sodium chloride can be added to the aqueous sulfonate after neutralization of the acid.

In order to obtain optimum fluidity, the viscosity of the aqueous sulfonate should be maintained below about 600 cp. In the case of an aqueous sulfonate which is about 22% active, that is, 22 weight percent sulfonate, the viscosity of the sulfonate can be lowered to the desired level by carrying out the neutralization in the presence of an amount of sodium chloride ranging from above about 3% to below about 5%, preferably about 4%, based on weight of sulfonate. At sodium chloride levels of about 3% or below, the aqueous sulfonate is highly viscous and flows poorly. At sodium chloride levels above about 5%, the aqueous sulfonate normally separates into two layers, which is undesirable. In carrying out the invention, it is preferable to maintain a homogeneous mixture.

The following examples are provided to illustrate the invention in accordance with the principles of the invention but are not to be construed as limiting the invention in any way, except as indicated by the appended claims. In the examples, viscosity was measured by a Brookfield Viscometer at 70° F.

EXAMPLES

Example 1

Preparation of Polypropylene Toluene Sulfonic Acid

A polypropylene toluene having an average molecular weight of about 316 and an average side chain length of about 16 carbon atoms was sulfonated continuously in a falling film sulfonator using 1.12 moles of sulfur trioxide per mole of alkylate. The alkylate was fed at 6.4 ml/min., and liquid sulfur trioxide (1.00 ml/min.) was vaporized by heating in a stream of nitrogen at 7 l/min. This sulfur trioxide-nitrogen stream was further diluted with nitrogen at 10 l/min. before contacting the alkylate. The reaction was carried out at about 60° C.

Example 2

This example demonstrates the neutralization of polypropylene toluene sulfonic acid in the absence of sodium chloride. To 163 g of water was added 10.3 g of 50 weight percent aqueous sodium hydroxide. A high-shear Eppenbach mixer was immersed in this solution at room temperature. The polypropylene sulfonic acid of Example 1 was added slowly while stirring at as high a speed as possible without ejecting the contents from the beaker. After 41.6 g of the acid had been added (about 85% of the acid required to neutralize the NaOH present), the resulting slurry, about 19% sulfonate, was too viscous to stir.

Example 3

To 162.5 g of water was added 0.5 g of sodium chloride (1% of sulfonate) and 10.3 g of 50 weight percent sodium hydroxide. Fifty (50) grams of polypropylene toluene sulfonic acid from Example 1 were added following the procedure of Example 2, until a pH of about 8 was reached. The resulting slurry, about 22% sulfonate, was difficult to stir.

Example 4

The procedure of Example 3 was repeated, except that 1.0 g of sodium chloride (2% of sulfonate) was employed. The resulting slurry was difficult to stir.

Example 5

The procedure of Example 3 was repeated, except that 1.5 g of sodium chloride (3% of sulfonate) was employed. The resulting slurry was easily mixed.

Example 6

The procedure of Example 3 was repeated, except that 2.0 g of sodium chloride (4% of sulfonate) was employed. The resulting slurry was very fluid.

Example 7

The procedure of Example 3 was repeated, except that 2.5 g of sodium chloride (5% of sulfonate) was employed. The resulting slurry was very fluid, but separated into two layers on standing.

Viscosity measurements for Examples 2 to 7 are provided in Table I.

TABLE I

| Example | Sulfonate, Wt. % | NaCl, Wt. % of Sulfonate | Brookfield Viscosity,[1] cp (70° F.) | Remarks |
|---|---|---|---|---|
| 2 | 19 | 0 | >500,000 | Too viscous to stir |
| 3 | 22 | 1 | >500,000 | Difficult to stir |
| 4 | 22 | 2 | 428,000 | Difficult to stir |
| 5 | 22 | 3 | 48,000 | Easily stirred |
| 6 | 22 | 4 | 250 | Very fluid |
| 7 | 22 | 5 | 400 | Fluid, but separated into 2 layers. |

[1]Spindle No. SC4-231 for Examples 2 to 5; Spindle No. SC4-18 for Examples 6 and 7

Example 8

This example demonstrates the addition of sodium chloride subsequent to neutralization of the polypropylene toluene sulfonic acid with aqueous sodium hydroxide.

A 24% active slurry of sodium polypropylene toluene sulfonate prepared as in Example 2 was highly viscous and very difficult to mix. To 100 g of this slurry was added 3.6 g of a 20 wt % solution of sodium chloride in water. The resulting 23.3% active slurry, containing 3 wt % sodium chloride based on active sulfonate, was easily mixed. The Brookfield viscosity was found to be 19,750 cp at 70° F., using Spindle No. SC4-231.

Example 9

A polypropylene xylene having an average molecular weight of about 333 and an average side chain length of about 16 carbon atoms was sulfonated using substantially the same procedure as in Example 1. The resulting polypropylene xylene sulfonic acid was neutralized with 50 weight percent aqueous sodium hydroxide to produce a 24.5% sodium polypropylene xylene sulfonate slurry.

Several aliquots of differing sodium chloride concentrations were prepared by adding a 10 percent aqueous sodium chloride solution and varying portions of water to the above 24.5% sodium polypropylene xylene sulfonate slurry. Resulting slurries of about 17 weight percent and 22 weight percent sulfonate were obtained. The Brookfield viscosity of these slurries was measured at 70° F., using Spindle No. SC4-231. The results are shown in Table II.

TABLE II

| Run No. | Sulfonate Wt. % | NaCl, Wt. % of Sulfonate | Brookfield Viscosity, cp (70° F.) |
|---|---|---|---|
| 1 | 17 | 0 | 23,700 |
| 2 | 22 | 0 | 92,000 |
| 3 | 22 | 1 | 33,300 |
| 4 | 22 | 2 | 18,700 |
| 5 | 22 | 3 | 4,000 |
| 6 | 22 | 4 | 540 |
| 7 | 22 | 5 | —(separated into two layers) |

Example 10

A linear alkyl toluene having a linear alkyl side chain of 15 to 18 carbon atoms was sulfonated using substantially the same procedures as in Example 1. The resulting linear alkyl toluene sulfonic acid was neutralized with 50 weight percent aqueous sodium hydroxide to produce a 19.5% sodium linear alkyl toluene sulfonate slurry.

Several aliquots of differing sodium chloride concentrations were prepared by adding a 20 percent aqueous sodium chloride solution and varying portions of water to the above 19.5% sodium linear alkyl toluene sulfonate slurry. The Brookfield viscosity of the resulting slurries was measured at 70° F., using Spindle No. SC4-231. The results are shown in Table II.

TABLE III

| Run No. | Sulfonate, Wt. % | NaCl Wt. % of Sulfonate | Brookfield Viscosity, cp (70° F.) |
|---|---|---|---|
| 1 | 19.5 | 0 | 700 |
| 2 | 19.2 | 2 | 228 |
| 3 | 19.0 | 3 | 136 |
| 4 | 18.8 | 4 | 87 |
| 5 | 18.6 | 5 | 62 |

What is claimed is:

1. A process for the preparation of a low viscosity aqueous alkyl toluene or alkyl xylene sulfonate from the alkyl toluene or alkyl xylene sulfonic acid obtained by the sulfur trioxide sulfonation of alkyl toluene or alkyl xylene having an average molecular weight of about 300 to 365 and a straight or branched alkyl side chain ranging from about $C_{12}$ to $C_{24}$ which comprises neutralizing the alkyl toluene or alkyl xylene sulfonic acid with aqueous sodium hydroxide in the presence of sufficient sodium chloride to lower the viscosity of the aqueous sodium alkyl toluene or alkyl xylene sulfonate produced to less than about 600 cp, while maintaining a homogeneous mixture.

2. The process according to claim 1, wherein the alkyl toluene or alkyl xylene sulfonic acid is neutralized with about 2 to 10 weight percent aqueous sodium hydroxide.

3. The process according to claim 1, wherein the alkyl toluene or alkyl xylene sulfonic acid is neutralized with about 3 to 6 weight percent aqueous sodium hydroxide.

4. The process according to claim 1, wherein the amount of sodium chloride present ranges from above about 3% to below about 5%, based on weight of sulfonate.

5. The process according to claim 4, wherein the amount of sodium chloride present is about 4%, based on weight of sulfonate.

6. The process according to claim 1, wherein the sulfonate is alkyl toluene sulfonate.

7. The process according to claim 6, wherein the sulfonate is polypropylene toluene sulfonate.

8. The process according to claim 6, wherein the sulfonate is linear alkyl toluene sulfonate.

9. The process according to claim 1, wherein the sulfonate is alkyl xylene sulfonate.

10. The process according to claim 9, wherein the sulfonate is polypropylene xylene sulfonate.

11. A process for the preparation of a low viscosity aqueous alkyl toluene or alkyl xylene sulfonate from the alkyl toluene or alkyl xylene sulfonic acid obtained by the sulfur trioxide sulfonation of alkyl toluene or alkyl xylene having an average molecular weight of about 300 to 365 and a straight or branched alkyl side chain ranging from about $C_{12}$ to $C_{24}$ which comprises neutralizing the alkyl toluene or alkyl xylene sulfonic acid with aqueous sodium hydroxide and subsequently adding sufficient sodium chloride to lower the viscosity of the aqueous sodium alkyl toluene or alkyl xylene sulfonate produced to less than about 600 cp, while maintaining a homogeneous mixture.

12. The process according to claim 11, wherein the amount of sodium chloride added ranges from above about 3% to below about 5%, based on weight of sulfonate.

13. The process according to claim 12, wherein the amount of sodium chloride added is about 4%, based on weight of sulfonate.

14. The process according to claim 11, wherein the sulfonate is alkyl toluene sulfonate.

15. The process according to claim 14, wherein the sulfonate is polypropylene toluene sulfonate.

16. The process according to claim 14, wherein the sulfonate is linear alkyl toluene sulfonate.

17. The process according to claim 11, wherein the sulfonate is alkyl xylene sulfonate.

18. The process according to claim 17, wherein the sulfonate is polypropylene xylene sulfonate.

* * * * *